United States Patent [19]

Hansen et al.

[11] Patent Number: 5,034,530
[45] Date of Patent: Jul. 23, 1991

[54] IMIDAZOQUINOXALINE COMPOUNDS AND THEIR PREPARATION AND USE

[75] Inventors: Holger C. Hansen; Frank Wätjen, both of Vaerlose, Denmark

[73] Assignee: Novo Nordisk A/S, Bagsvaerd, Denmark

[21] Appl. No.: 363,585

[22] Filed: Jun. 8, 1989

[30] Foreign Application Priority Data

Jun. 14, 1988 [DK] Denmark .............................. 3220/88

[51] Int. Cl.$^5$ .......................................... C07D 471/02
[52] U.S. Cl. .................................. 544/346; 544/353; 544/366
[58] Field of Search .............. 544/345, 353, 366, 375, 544/346, 347; 514/259

[56] References Cited

U.S. PATENT DOCUMENTS 4,440,929 4/1984 Lee et al. .............................. 544/346
4,774,245 9/1988 Wätjen .............................. 544/343

Primary Examiner—Jose G. Dees
Assistant Examiner—Deborah D. Carr
Attorney, Agent, or Firm—Gordon W. Hueschen

[57] ABSTRACT

New imidazoquinoxaline compounds having the general formula

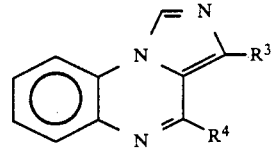

wherein
$R^3$ is

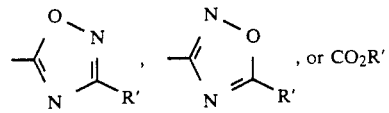

, or $CO_2R'$ wherein R' is $C_{1-6}$-alkyl, which may be straight or branched, $C_{3-7}$-cycloalkyl or phenyl; and
$R^4$ is hydrogen or $C_{1-6}$-alkyl; and 5-N-oxides thereof.

The compounds are useful in psychopharmaceutical preparations as anticonvulsants, anxiolytics, hypnotics, and in improving the cognitive function of the brain of mammals.

7 Claims, No Drawings

IMIDAZOQUINOXALINE COMPOUNDS AND THEIR PREPARATION AND USE

The present invention relates to therapeutically active imidazoquinoxaline compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of imidazoquinoxaline compounds have strong affinity for the benzodiazepine receptors which make them useful in psychopharmaceutical preparations.

Accordingly, it is an object of the invention to provide such novel imidazoquinoxaline compounds.

The imidazoquinoxaline compounds of the invention have the general formula I

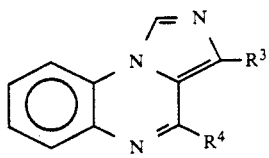

wherein
$R^3$ is

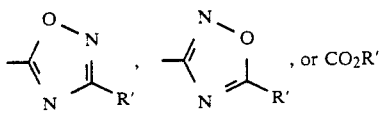

wherein R' is $C_{1-6}$-alkyl, which may be straight or branched, $C_{3-7}$-cycloalkyl or phenyl; and
$R^4$ is hydrogen or $C_{1-6}$-alkyl; and 5-N-oxides thereof.

The invention also relates to a method of preparing the above mentioned compounds. This method comprises:

a) reacting a compound of formula II

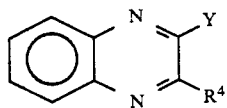

wherein $R^4$ has the meaning set forth above and wherein Y is a leaving group, with a compound having the formula III $$CN-CH_2-R^3 \qquad (III)$$

wherein $R^3$ has the meaning set forth above, to form a compound of the invention, or b) reacting a reactive derivative of a compound having the general formula IV

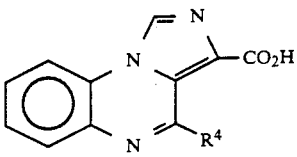

wherein $R^4$ has the meaning set forth above, with a compound having the general formula V $$R'-C(=NOH)NH_2 \qquad (V)$$

wherein R' has the meaning set forth above to form a compound of the general formula I wherein $R^3$ is

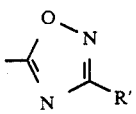

wherein R' has the meaning set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, $-OP(O)(OR)_2$ wherein R is lower-alkyl or $-OP(O)(NR'R'')$ wherein R' and R'' each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available organic compounds and by using well known synthetic methods and as described in Synthesis, Vol. 10, pp. 681-682.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of flunitrazepam to benzodiazepine receptors in a living brain to be reduced to 50% of the control value.

Such an in vivo test is carried out as follows:

Principle. Twenty minutes after a dose of $^3H$-flunitrazepam ($^3H$-FNM) (200 $\mu$Ci/kg, i.v.) the amount of specific $^3H$-FNM binding to brain benzodiazepine receptors has reached its maximal value. This specific binding of $^3H$-FNM can be partly or completely prevented by simultaneous or prior administration of pharmacologically active benzodiazepines and by some benzodiazepine-like agents (Chang and Snyder, Eur.J. Pharmacol. 48, 212-218 (1978)).

Test procedure. Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR, 18-22 grams) are injected with the test substance at 100 mg/kg intraperitoneally. Fifteen minutes after test substance administration the mice are challenged with 4 μCi intravenously of $^3$H-FNM (70-90 Ci/mole) in 200 μl physiological saline. Twenty minutes after $^3$H-FNM administration mice are sacrificed by decapitation, the forebrains rapidly excised (within 30 sec) and homogenized in 12 ml of icecold 25 mM $KH_2PO_4$, pH 7.1, using an Ultra-Turrax homogenizer fitted with an N 10 shaft. Two aliquots of 1 ml are immediately filtered through Whatman GF/C glassfibre filters and washed with $2 \times 5$ ml of the above mentioned buffer. The amounts of radioactivity on the filters are determined by conventional scintillation counting. One group of untreated mice serves as control. One to three mice are injected with 25 μg/kg clonazepam i.p. 30 minutes before $^3$H-FNM to determine the amount of non-specific $^3$H-FNM binding, which should be between 8-15% of total binding. When doses of 100 mg/kg inhibit more than 50% of specific $^3$H-flunitrazepam binding; test substances are administered in doses, which are factors of 3.16 times lower than 100 mg/kg. The $ED_{50}$ for a test substance is defined as that dose which inhibits 50% of specific $^3$H-FNM binding. Specific binding is the amount of binding in controls minus the amount binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25-75%:

$$ED_{50} = (\text{administered dose}) \times \frac{1}{\left[\frac{C_o}{C_x} - 1\right]} \text{ mg/kg}$$

where $C_o$ is specific binding in controls and $C_x$ is specific binding in mice treated with test substance.

Test results obtained by testing some compounds of the invention will appear from the following table I.

TABLE 1

| Compound | $ED_{50}$ (mg/kg) |
| --- | --- |
| 8 | 1.8 |
| 7 | 1.3 |
| 10 | 3.5 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05-100 mg in a pharmaceutically-acceptable carrier per unit dosage.

A typical tablet which may be prepared by conventional tabletting techniques contains:

| | |
| --- | --- |
| Active compound | 1.0 mg |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the socalled benzodiazepin receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1

Ethyl 4-methyl-imidazo[1,5-a]quinoxaline-3-carboxylate

3-Methyl-2-quinoxalinol (2.84 g, 18 mmol) was dissolved in dry DMF (40 ml) and charged with sodium hydride (55% oil dispersion, 1.0 g, 23 mmol). The resulting solution was cooled under nitrogen to −20° C., whereafter chlorodiethylphosphate (3.3 ml, 23 mmol) was added. The reaction mixture was allowed to reach room temperature, and was then added a −30° C. cold solution of ethyl isocyanoacetate (2.6 g, 23 mmol) and potassium t-butoxide (2.6 g, 23 mmol) in dry DMF (25 ml). The mixture was stirred for 45 min. at ambient temperature, whereafter acetic acid (3 ml) was added. The crystalline precipitate was collected by filtration, rinsed with DMF and water and dried, yielding 2.5 g of the title compound. M.p. 192°-193° C. (Compound 1)

An additional amount of product precipitated when the filtrate was evaporated, and the resulting residue was stirred with a mixture of water (100 ml) and ethyl acetate (25 ml).

In a similar manner the following compounds were prepared:
Ethyl imidazo[1,5-a]quinoxaline-3-carboxylate. M.p. 195°-196° C., from 2-quinoxalinol and ethyl isocyanoacetate. (Compound 2)
Isopropyl imidazo[1,5-a]quinoxaline-3-carboxylate. M.p. 205°-206° C., from 2-quinoxalinol and isopropyl isocyanoacetate. (Compound 3)
Tert-butyl imidazo[1,5-a]quinoxaline-3-carboxylate. M.p. 187°-190° C., from 2-quinoxalinol and tert-butyl isocyanoacetate. (Compound 4)
Isopropyl 4-methyl-imidazo[1,5-a]quinoxaline-3-carboxylate. M.p. 182°-183° C., from 3-methyl-2-quinoxalinol and isopropyl isocyanoacetate. (Compound 5)
Tert-butyl 4-methyl-imidazo[1,5-a]quinoxaline-3-carboxylate. M.p. 176°-177° C., from 3-methyl-2-quinoxalinol and tert-butyl isocyanoacetate. (Compound 6)
3-(5-Cyclopropyl-1,2,4-oxadiazol-3-yl)—4-methyl-imidazo[1,5-a]quinoxaline. M.p. 165°-167° C., from 3-methyl-2-quinoxalinol and 5-cyclopropyl-3-isocyanomethyl-1,2,4-oxadiazole. (Compound 7)
4-Methyl-3-(5-methyl-1,2,4-oxadiazol-3-yl)-imidazo[1,5-a]quinoxaline. M.p. 192°-193° C., from 3-methyl-2-quinoxalinol and 3-isocyanomethyl-5-methyl-1,2,4-oxadiazole. (Compound 8)

EXAMPLE 2

4-Methyl-3-(3-methyl-1,2,4-oxadiazol-5-yl)imidazo[1,5-a]quinoxaline (Compound 9)

Sodium (0.1 g) was dissolved in dry ethanol (100 ml). Ethyl 4-methyl-imidazo[1,5-a]quinoxaline-3-carboxylate (1.0 g, 4 mmol), acetamide oxime (1.5 g, 20 mmol) and crushed molecular sieves (4Å, 5 g) were added. After the mixture had been refluxed for 9 h it was cooled to 40° C. and dichloromethane (200 ml) was added. The molecular sieves were removed by filtration through a pad of celite, and the filtrate was evaporated in vacuo. The residue was suspended in water (50 ml) and the crystalline precipitate of the title compound was collected by filtration and dried. M.p. 255°-256°C.

In the same manner the following compounds were prepared:
3-(3-Cyclopropyl-1,2,4-oxadiazol-5-yl)-4-methyl-imidazo[1,5-a]quinoxaline. M.p. 188°-189° C., from ethyl 4-methylimidazo[1,5-a]quinoxaline-3-carboxylate and cyclopropancarboxamide oxime. (Compound 10)
3-(3-methyl-1,2,4-oxadiazol-5-yl)-imidazo[1,5-a]quinoxaline. M.p: 269°-270° C., from ethyl imidazo[1,5-a]quinoxaline-3-carboxylate and acetamide oxime. (Compound 11)
3-(3-cyclopropyl-1,2,4-oxadiazol-5-yl)-imidazo[1,5-a]quinaline. M.p. 208°-210° C., from ethyl imidazo[1,5-a]quinoxaline-3-carboxylate and cyclopropancarboxamide oxime. (Compound 12)
4-Methyl-3-(3-phenyl-1,2,4-oxadiaxol-5-yl)-imidazo[1,5-a]quinoxaline. M.p. 272°-273° C., from ethyl 4-methyl-imidazo 1,5-a]quinoxaline-3-carboxylate and benzamide oxime. (Compound 13)

EXAMPLE 3

4-Methyl-3-(3-methyl-1,2,4-oxadiazol-5-yl)-imidazo[1,5-a]quinoxaline-5-oxide (Compound 14)

4-Methyl-3-(3-methyl-1,2,4-oxadiazol-5-yl)-imidazo[1,5-a]quinoxaline (0.36 g, 1.4 mmol) and 55% 3-chloroperbenzoic acid (0.5 g, 1.6 mmol) was dissolved in dichloromethane (100 ml). After 18 h at room temperature an addidional amount of oxidizing agent (0.5 g) was added, and the solution was heated to reflux for 2 h. Then the reacation mixture was cooled to room temperature and extracted with 10% aqueous potassium carbonate (50 ml). The organic layer was dried over sodium sulphate and evaporated. The residue was suspended in ether and the title compound was collected by filtration. Purification by column chlomatography (silica gel/ethyl acetate-methanol 9:1) gave a product with m.p. 239°-243° C.

In the same manner oxidation of 3-(5-cyclopropyl-1,2,4-oxadiazol-3-yl)-4-methyl-imidazo[1,5-a]quinoaline gave 3-(5-cyclopropryl-1,2,4-oxadiazol-3-yl)-4-methyl-imidazo[1,5-a]quinoxaline-5-oxide. M.p. 210°-212° C. (Compound 15)

We claim:

1. Imidazoquinoxaline compounds having the formula I

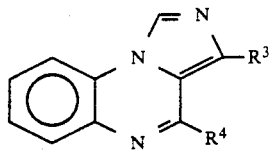

wherein
R³ is

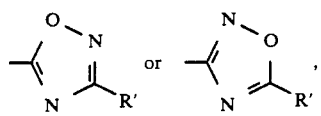

wherein R' is $C_{1-6}$-alkyl, which may be straight or branched, $C_{3-7}$-cycloalkyl or phenyl; and
R⁴ is hydrogen or $C_{1-6}$-alkyl; and 5-N-oxides thereof.

2. A compound of claim 1 which is 3-(5-cyclopropyl-1,2,4-oxadiazol-3-yl)-4-methyl-imidazo[1,5-a]quinoxaline 3. A compound of claim 1 which is 4-methyl-3-(5-methyl-1,2,4-oxadiazol-3-yl)-imidazo[1,5-a]quinoxaline 4. A pharmaceutical composition useful in the treatment of a central nervous system ailment selected from convulsion and anxiety comprising an amount of a compound of claim 1 which is effective for the alleviation of such disorder together with a pharmaceutically-acceptable carrier or diluent.

5. A pharmaceutical composition according to claim 4 wherein it is in the form of an oral dosage unit containing 1–100 mg of the active compound.

6. A method of treating a central nervous system ailment selected from convulsion and anxiety in a subject in need of such treatment comprising the step of administering to said subject an amount of a compound of claim 1 which is effective for the alleviation of such ailment.

7. A method of treating a central nervous system ailment selected from convulsion and anxiety in a subject in need of such treatment comprising the step of administering to said subject an amount of a compound of claim 1 which is effective for the alleviation of such ailment in the form of a pharmaceutical composition thereof, in which it is present together with a pharmaceutically-acceptable carrier or diluent.

* * * * *

UNITED STATES PATENT AND TRADEMARK OFFICE
CERTIFICATE OF CORRECTION

PATENT NO. : 5,034,530

DATED : Jul. 23, 1991

INVENTOR(S) : Holger C. Hansen, Frank Wätjen

It is certified that error appears in the above-identified patent and that said Letters Patent is hereby corrected as shown below:

Column 5, line 1; "socalled" should read -- so-called --.
Column 6, approximately line 12; move the closing bracket "]" at the beginning of line 12 and insert at the end of line 11 after "5" and before the dash.
Column 6, line 42; "-imidazo 1,5-a]" should read -- -imidazo[1,5-a] --.
Column 6, line 53; "addidional" should read -- additional --.
Column 6, line 55; "reacation" should read -- reaction --.
Column 6, line 60; "chlomatography" should read -- chromatography --.
Column 6, line 64; "quinoaline" should read -- quinoxaline --.
Column 6, line 65; "-cyclopropryl- should read -- cyclopropyl- --.

Signed and Sealed this

Twenty-third Day of February, 1993

*Attest:*

STEPHEN G. KUNIN

*Attesting Officer*   Acting Commissioner of Patents and Trademarks